United States Patent [19]
Barnard et al.

[11] Patent Number: 5,483,337
[45] Date of Patent: Jan. 9, 1996

[54] SPECTROMETER WITH SELECTABLE RADIATION FROM INDUCTION PLASMA LIGHT SOURCE

[76] Inventors: Thomas W. Barnard, 36 Kramer La., Weston, Conn. 06883; Michael I. Crockett, 7 White Oak Farm Rd., Newtown, Conn. 06470; Michael W. Hucks, 30 Flint Ridge Rd., Monroe, Conn. 06468

[21] Appl. No.: 325,735

[22] Filed: Oct. 19, 1994

[51] Int. Cl.$^6$ .............................. G01J 3/30; G01N 21/73
[52] U.S. Cl. ........................... 356/316; 356/319; 356/328
[58] Field of Search ..................................... 356/316, 318, 356/319, 323, 325, 326, 328

[56] References Cited

U.S. PATENT DOCUMENTS

| | | | |
|---|---|---|---|
| 4,182,574 | 1/1980 | Quillfeldt | 356/318 |
| 4,261,638 | 4/1981 | Wagner . | |
| 4,326,802 | 4/1982 | Smith, Jr. et al. | 356/316 |
| 4,545,680 | 10/1985 | Smith, Jr. | 356/319 |
| 4,622,468 | 11/1986 | Stefanski et al. | 250/458.1 |
| 4,766,287 | 8/1988 | Morrisroe et al. | 219/121.52 |
| 4,820,048 | 4/1989 | Barnard | 356/328 |
| 5,005,934 | 4/1991 | Curtiss . | |
| 5,343,289 | 8/1994 | Crawford et al. | 356/328 |

*Primary Examiner*—Vincent P. McGraw
*Assistant Examiner*—K. P. Hantis
*Attorney, Agent, or Firm*—Edwin T. Grimes; Herbert S. Ingham

[57] ABSTRACT

An atomic emission spectrometer includes an induction coupled plasma generator and a detector system for detecting the radiation relative to spectral wavelength. A first mirror is on the longitudinal axis of the generator to receive axial radiation therefrom. A second mirror is disposed laterally from the generator so as to reflect radial radiation therefrom parallel to the longitudinal axis toward a third mirror disposed laterally from the longitudinal axis. The third mirror passes the radiation to a fourth mirror positioned adjacent to the axial radiation without interfering therewith so as to reflect the radial radiation to the first mirror. The first mirror is rotated to a first orientation to reflect the axial radiation into the detector system, or to a second orientation to reflect the radial radiation into the detector system.

12 Claims, 3 Drawing Sheets

SPECTROMETER WITH SELECTABLE RADIATION FROM INDUCTION PLASMA LIGHT SOURCE

FIELD OF INVENTION

This invention relates to an atomic emission spectrometer having an induction coupled plasma source of light radiation, and particularly to such a spectrometer in which the radiation detected is selectable from radiation emitted axially or radially from the plasma source.

BACKGROUND OF THE INVENTION

A common type of spectrometer for inorganic analysis is an atomic emission spectrometer having an induction coupled plasma ("ICP") source of light radiation. The induction plasma generator utilizes an electrical induction coil to deliver high power at high frequency to excite a gas into a plasma. A nebulized sample material is injected into the plasma where it becomes disassociated into atoms which are excited in the plasma to emit radiation including spectral lines characteristic of the atomic elements in the sample. An example of such an induction plasma system is disclosed in U.S. Pat. No. 4,766,287 (Morrisroe et al).

Light radiation from the ICP is passed into a detector system that typically incorporates a monochromator or polychromator. A monochromator passes a selected wavelength of radiation to a detector, as disclosed in U.S. Pat. No. 4,326,802 (Smith et al). A polychromator disperses the radiation into a band or multiplicity of wavelengths that are detected. An example of a precision polychromator is an echelle system with crossed gratings to produce a two-dimensional display of spectral lines as disclosed in U.S. Pat. No. 4,820,048 (Barnard). The spectral lines are focused onto a detector formed from a two dimensional solid state charge transfer device which effects signals proportional to the intensity of the corresponding lines. A computer processes the signal information, corrects for background, applies calibration, and displays the results in the form of concentrations of atomic elements in the sample.

The ICP typically is mounted to the spectrometer so that radiation emitted radially from the ICP is directed into the detector system, as illustrated in the aforementioned U.S. Pat. No. 4,326,802. In the example disclosed therein, a mirror is receptive of the radial radiation, the mirror and associated lens components having an adjustable position longitudinally to optimize the location of atomic emissions.

The ICP also has been mounted longitudinally so as to direct radiation from along the central axis of the ICP into the detector system. Radial emission has been preferred for analytical accuracy, because the axial radiation has more self absorption along the longer longitudinal path in the plasma plume, and there are chemical interferences in the axial radiation from the fringe zone in the plasma where the sample material is not maximally atomized. However, the axial radiation has a longer emission path which provides greater sensitivity for low emission levels. Thus the longitudinal mounting for the ICP is often desirable when there are low levels of an atomic element in the sample being tested. Where flexibility has been desired for selecting either higher accuracy or higher sensitivity, it has been necessary to change the mounting of the ICP, which generally has not been a practical procedure on a repetitive basis, or to utilize two spectrometers which is costly.

Various systems have been used for optical switching. For example, the aforementioned U.S. Pat. No. 4,326,802 discloses the use of a mirror positionable by rotation to select between the radial radiation from the ICP and a calibration source of light. U.S. Pat. No. 4,622,468 (Stefanski et al) illustrates the use of beam splitters and shutters in a fluorescence detection system with a halogen lamp light source. A concave mirror is rotatable on an offset axis parallel to the central axis for switching as disclosed in U.S. Pat. No. 4,261,638 (Wagner). Other optical switches include rotating periscopes and Porro reflectors such as disclosed in U.S. Pat. No. 5,005,934 (Curtiss).

However, none of the foregoing references teaches selection of either radial or axial radiation from an ICP. Therefore, an object of the invention is to provide an improved atomic emission spectrometer having a capability for selecting either radial or axial radiation from an ICP. Another object is to provide an improved ICP atomic emission spectrometer having selectivity between maximum accuracy and maximum sensitivity. A further object is to provide such a spectrometer with speed and convenience in making the selection.

SUMMARY OF THE INVENTION

The foregoing and other objects are achieved, at least in part, in an atomic emission spectrometer comprising an induction coupled plasma generator for effecting light radiation, a detector means for detecting the radiation relative to spectral wavelength, and an optical apparatus arranged cooperatively with the plasma generator and the detector means to pass radiation emitted from the plasma generator to the detector means. The radiation from the generator includes axial radiation emitted along the longitudinal axis of the generator, and radial radiation emitted from the plasma generator generally normal to the longitudinal axis. The optical apparatus comprises optical selection means for selectively passing either the axial radiation or the radial radiation to the detector means.

In a preferred embodiment, the axial radiation or the radial radiation is preselected as a primary radiation having a linear path line and the other is a secondary radiation. The selection means comprises a rotatable first reflector spaced from the plasma generator on the path line so as to be receptive of the primary radiation. The selection means further comprises reflector means disposed to be receptive of the secondary radiation and pass the same to the first reflector at an angle different than that of the primary radiation. The first reflector is rotated to a first orientation or to a second orientation, the first orientation being to reflect the primary radiation into the detector means, and the second orientation being to reflect the secondary radiation into the detector means. More preferably, the first reflector is spaced from the plasma generator on the longitudinal axis, whereby the axial radiation is predetermined as the primary radiation and the radial radiation is predetermined as the secondary radiation.

In a more specific embodiment, the reflecting means comprises a series of reflectors for the radial radiation. A second reflector is disposed laterally from the path line so as to reflect secondary radiation from the plasma generator into a direction generally parallel to the path line toward the first reflector. A third reflector is disposed laterally from the path line so as to reflect the radiation from the second reflector toward a central point proximate the path line between the plasma generator and the first reflector. A fourth reflector is disposed at the central point adjacent to the primary radiation without substantially interfering therewith so as to reflect the secondary radiation from the third reflector to the first reflector.

DETAILED DESCRIPTION OF THE INVENTION

Figure 1:
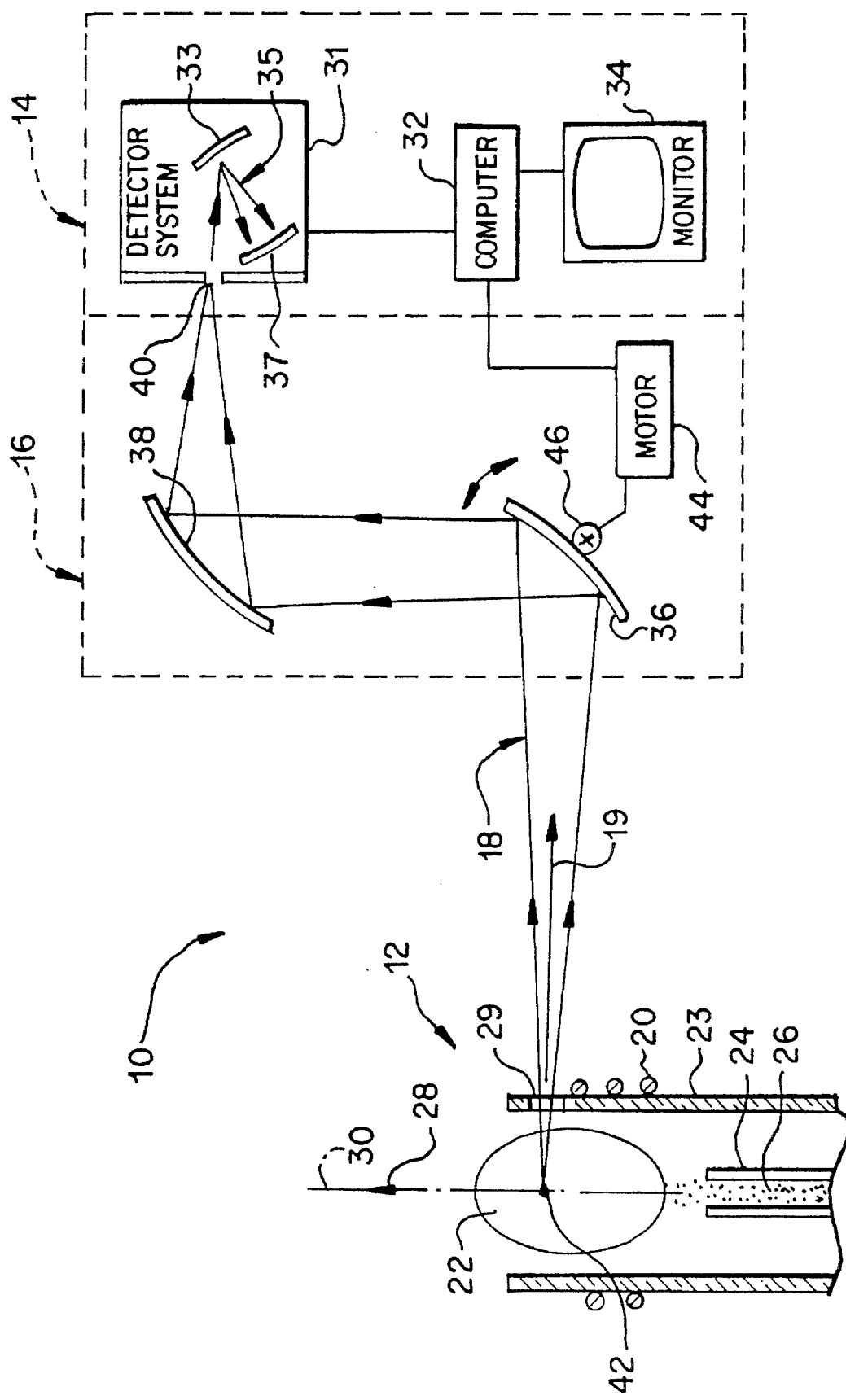
FIG. 1 is a drawing of a conventional atomic emission spectrometer, including a partial longitudinal section of an induction coupled plasma generator, and a schematic drawing of a system for detecting light radiation and an optical apparatus for passing radiation from the generator to the system.

FIG. 1 schematically illustrates a conventional atomic emission spectrometer 10 for utilizing the invention. An example of such an instrument is a model Optima™ 3000 spectrometer sold by The Perkin-Elmer Corporation. Three general components of the instrument are an induction coupled plasma generator 12 which effects light radiation, a detector means 14 for detecting the radiation relative to spectral wavelength, and an intermediately located optical apparatus 16 configured to pass and focus the radiation 18 along a path 19 from the plasma generator to the detector system.

The induction plasma generator 12 ("ICP") is a conventional or other desired type that utilizes an induction coil 20 to excite a gas into a plasma 22 in a region within or slightly beyond the end of a quartz tube 23. The generator includes an injector 24 for injecting a nebulized sample material 26 into the plasma. The material becomes disassociated to atoms which are excited in the plasma to emit radiation including spectral lines characteristic of the atomic elements in the sample. An example of such an ICP generator and an associated high frequency power supply are disclosed in the aforementioned U.S. Pat. No. 4,766,287 which is incorporated herein by reference. For the purpose of the present invention, the sample injector may be adjustable as disclosed in the latter patent, or fixed. The type of power generator is not important herein and, for example, may be a conventional circuit with a floating oscillator whose frequency matches that of the LC circuit that includes the ICP coil. The ICP is generally axi-symmetric except for the spiral coil 20. Radiation is emitted from the plasma region in all directions including axially 28 along the longitudinal axis 30 of the generator and radially in a span of directions generally normal to the longitudinal axis, including the radial component 18 being detected via an opening 29 in the tube 23. The light radiation to be detected is generally within the range of infrared, visible and ultraviolet.

The detector means 14 includes a detector system 31 which is any conventional or other desired type used for the purpose of the spectrometer, typically incorporating a monochromator or polychromator, the details not being critical to the present invention. A suitable example is the precision polychrometer of the aforementioned Optima 3000 having an echelle grating system 33 (shown only schematically in FIG. 2) with crossed gratings (and/or one or more prisms) to produce a two-dimensional display of spectral lines, substantially as disclosed in the aforementioned U.S. Pat. No. 4,820,048 which is incorporated herein by reference. The detector system includes a two dimensional solid state "CCD" detector 37 or the like which effects signals proportional to the intensity of the corresponding lines. A computer 32 processes the signal information, corrects for background and, with calibration, displays the results on a monitor 34 and/or printer as concentrations of atomic elements in the sample. The optical dispersion elements and the detector are not shown in detail herein as they are explained in the aforementioned patent. (As used herein and in the claims, the term "detector means" encompasses the group of components for wavelength filtering or dispersion, one or more detectors of the filtered or dispersed radiation, optical elements for reflecting and focusing in the associated train, and means for processing and displaying results.)

As indicated above, an intermediately located optical apparatus 16 passes radiation from the plasma 22 to the detector system 31. In a conventional spectrometer (e.g. the aforementioned Perkin-Elmer Optima 3000), radiation detected from the plasma is either radial radiation 18 along path line 19 from an ICP generator oriented at right angles (as shown in FIG. 1), or axial radiation 28 from an axially aligned generator (not shown in FIG. 1). In either case, a mirror 36 oriented at about 45° is receptive of the radiation. The mirror reflects the radiation 39 to a concave mirror 38, also at 45°, that together with mirror 36 focusses the radiation as an image of a predetermined emission point 42 in the plasma source to an aperture 40 (a slit vertical to the drawing in the present example) located at the entrance to the detector system. The mirror 36 may be flat but preferably is concave, most preferably as a concave toroid to equalize focussing from the horizontal and vertical planes (the drawing being horizontal). Also, the concave mirror 38 should be a concave toroid for the same reason. The "emission point" 42 is actually a central point in finite lengths of emission zones in the plasma that radiate into the axial and radial paths.

For precision the mirror 36 may have associated therewith a stepper motor 44 for rotating the mirror in small increments about an axle 46 in or near the effective plane of the mirror so as to align or select a point of the radiation from the plasma to focus onto the slit. A second motor (not shown) is provided to rotate the mirror on an orthogonal axis for further alignment. The motors are advantageously controlled by the computer 32 of the spectrometer to optimize the signals, either automatically or with operator input. In the present example, the orientation of the first mirror 36 is nominally 45° with small corrections for alignment, but may be at another angle depending on the relative locations of the plasma generator 12 and the concave mirror In another alternative, the first mirror may be more concave for focussing at the slit, with the mirror 38 flat. Or the concave mirrors 36, 38 may be replaced by one or more lenses in the optical path. Other folding mirrors (not shown) may be used as needed or desired.

According to the invention (FIG. 2), an optical apparatus 48 is disposed between the plasma generator 12 and the detector means 14 to selectively direct either the axial radiation 28 on the longitudinal axis 30 or a beam of radial radiation 18 along a radial path 19, from the generator to the detector system 31. This apparatus 48 replaces the intermediate optics 16 of FIG. 1, although preferably the same optical elements (e.g. mirrors 38) are utilized. (Where components and features are preferably the same as in FIG. 1, the same numeral designations are used herein.) The axial radiation 28 passes directly from the plasma 22 to first mirror 36 which reflects the radiation to mirror 38 and thence to the slit. Advantageously mirror 36 is the same as that in the conventional instrument (FIG. 1) and has associated therewith the stepper motor 44 to align the radiation input to the slit. However, manual rotation of the mirror with a knob or lever is an alternative.

In a preferred embodiment of the optical apparatus 48, a second mirror 50 is disposed laterally from the plasma generator 12, preferably oriented at 45°, so as to reflect radial radiation 18 via opening 29 into a path 52 parallel (or at least generally parallel) to the longitudinal axis 30 and generally in the direction of the first mirror 36 (as distinguished from oppositely). A third mirror 54 is disposed laterally from the longitudinal axis, also preferably at 45° and at the same distance and radial direction from the axis as the second mirror, so as to reflect the radiation from the second mirror into a path 56 on a centerline 64 toward a central point 58 proximate (but not on) the longitudinal axis 30 between the plasma generator and the first mirror. (The examples herein utilize planar mirrors to reflect the radiation, but prisms such as right angle prisms with internal reflecting surfaces that are substantially equivalent to mirrors may be used as reflectors.)

A fourth mirror 60 is disposed adjacently to the axial radiation 28 so as to reflect the radial radiation on path 56 from the third mirror 54 into a path 62 toward the first mirror 36. The central point 58 is defined to be on the mirror 60 and is determined by the intersecting centerlines 64, 66 of the radial radiation before and after the fourth mirror. The fourth mirror should be as close as possible to the apertured beam of axial radiation 28, without the mirror substantially interfering with the axial radiation being passed directly to the first mirror 36. To achieve this, mirror 60 should be outside of, or at least not cut off more than about 10% of the apertured axial beam 28. The fourth mirror also should be as close to the plasma generator 12 as reasonable practical without being significantly heated thereby to minimize the angle explained below.

An angled line 66 is defined from the point 58 to an axial point 68 of the intersection of the axis 30 and the first mirror 36, and this line should be at a minimal angle A without the mirror 60 interfering. If the fourth mirror receives radiation from the third mirror 54 on a line 64 normal to the axis 30, the fourth mirror will be almost 45° to the axis, but at an actual angle that corrects for the offset from the axis. Most preferably the radiation from the third mirror crosses the longitudinal axis 30 to reach the fourth mirror, and all of the optical axes of the axial and radial paths of radiation to the slit should lie in a common plane (the plane of the drawing). However, in a broader aspect of the invention, the paths may deviate somewhat from this, and the 45° mirror orientations are not critical. Also, other intermediate folding mirrors may be utilized as desired; for example the radiation may be passed from one of the foregoing mirrors to the next via such further mirrors.

To achieve the dual selection, the first mirror is rotated on its axle 46 by the motor 44 to either of two orientations, for example under control of the computer 32 with operator input as desired. In a first orientation (position of mirror as shown) the mirror reflects the axial radiation 30 from the plasma 22 into the detector system 14, and in a second orientation 70 (broken lines) the radial radiation on its centerline 66 from the fourth mirror 60 is reflected into the detector system. The same mounting and control for the first mirror is advantageously utilized as for a spectrometer that already has an alignment facility without a dual selection (FIG. 1), and the two orientations for selection may be fine tuned for alignment.

The angle A of the fourth mirror from the axis 30 should be substantially as small as possible, desirably between about 1° and 10°, and preferably between about 2° and 5°, so as to minimize optical path differences and optical aberrations and to utilize a small motor drive range that may be in place for aligning the first mirror. For example, an angle of 3.3° for the line to the central point of the fourth mirror is practical and provides for mirror switching angle B (half of angle A) of only 1.65°. This is readily achieved with a spacing of 30 cm between the plasma generator and the first mirror, 8 cm between the generator and the fourth mirror, and an axial radiation beam width of 1 cm at the fourth mirror.

Examples of other dimensions are 38 cm between the concave first mirror 36 and the concave mirror 38, and 10 cm between the mirror 38 and the aperture 40 (such distances being on centerlines). The second and third mirrors 50, 54 are located conveniently 8 cm from the longitudinal axis, for a plasma generator tube 23 that is 2 cm in diameter. To focus the emission point 42 to the aperture 40, for the foregoing dimensional locations, toroidal radii of curvature, respectively in the vertical plane and horizontal plane (horizontal being the plane of the drawing), for the mirror 36 are 35.23 cm and 56.88 cm, and for the mirror 38 are 18.14 cm and 39.00 cm.

The axial radiation has a first optical path length extending along the axis from the predetermined emission point 42 in the plasma to the entrance aperture (slit) 40. The radial radiation has a second path length from the same point 42 to the aperture via the intermediate mirrors, the second path length being longer than the first. The mirrors 36, 38 (or substitute lenses) constitute a common means for focussing either the axial radiation or the radial radiation to the slit. The difference between the optical path lengths of the axial and radial radiations should be compensated to provide for focussing of the point 42 in the plasma by either path onto the entrance slit 40 of the detector system 31, such that the emission point and the aperture are conjugate foci for both the axial radiation and the radial radiation. This is achieved preferably by utilizing a fourth mirror that is slightly convex. The mirror may be spherically convex, but more accurately has a toroidal surface with a focal length longer in the horizontal plane (of the drawing) calculated as the square root of two multiplied by the focal length in the vertical planes which is set to give the required focal path length. For the dimensional locations set forth above, toroidal radii of curvature for the convex fourth mirror 60 are 152.9 mm and 419.7 mm. Other means may be used for the compensation, such as making one of the other intermediate mirrors convex, or inserting a convex lens in the second train. Alternatively, the axial radiation focal length may be shortened with a concave lens between the plasma 22 and the first mirror.

In addition to having means for selecting the first or second orientations, the first mirror is desirably further rotatable to finely adjust its first orientation on the axle 46 so as to align the axial radiation into the aperture 40, so that the selected emission point is on (or selectably proximate) the axis 30. This is the same type of adjustment as for the conventional instrument (FIG. 1). Similarly, the second orientation also should allow fine adjustment to select position from a range 74 along the axis of the emission point of radiation for the radial radiation, the selected point being where the sample material is optimally atomized and excited. These adjustments are achieved by the motor 44 preferably by control of the computer 32, either by a program with feedback to maximize a detector signal or with operator input. However, manual adjustments with a micrometer knob or the like are alternative.

A mirror housing 76 is provided with windows 80 of fused quartz or the like at entrance locations for the radiation, to contain nitrogen or other inert gas to minimize any absorption of radiation by oxygen in the extra path length of the radial radiation. The housing at an exit aperture 81 is connected by a hermetic seal 83 to the housing 82 (or housings) containing all other optical components (including the mirrors 36, 38) leading to and forming the detector system 31. These housings are filled with gas such as nitrogen or argon but not oxygen to avoid absorption of radiation. A small bleed outlet for the gas can be provided at the entrance apertures 80. Heat from the plasma gas to the housing is blocked by a conventionally disposed flat nozzle (not shown, located above the plane of the drawing) to provide a cross fan of nitrogen gas normal to the axis 30 about 2–3 cm from the end of the plasma coil 20.

Figure 2:
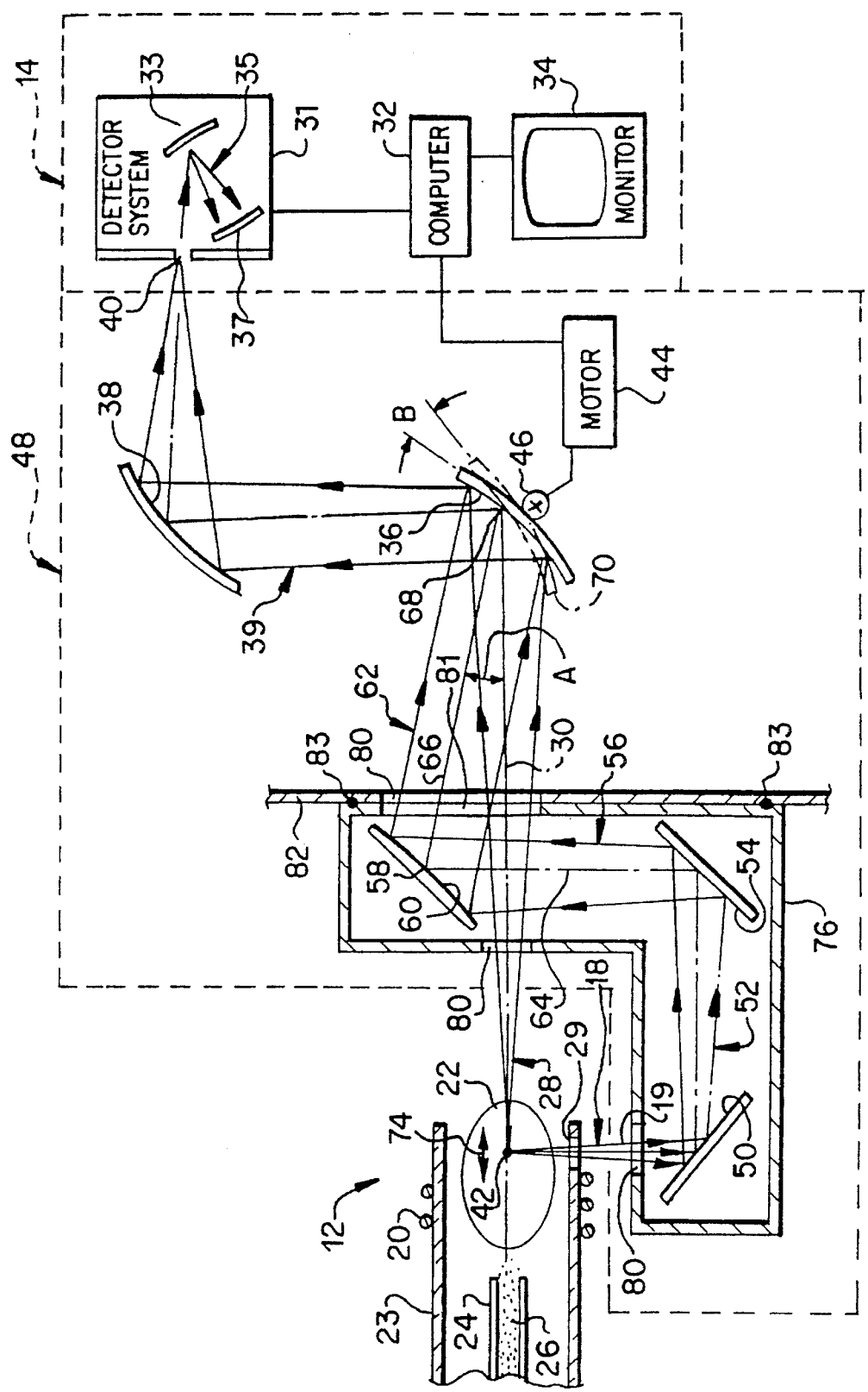
FIG. 2 is a drawing of an atomic emission spectrometer according to the invention, including a partial longitudinal section of an induction coupled plasma generator, and a schematic drawing of a system for detecting light radiation and an optical apparatus for passing radiation from the generator to the system.

Although the foregoing apparatus based on FIG. 2 represents a preferred embodiment for the intermediate optical apparatus, other means may be provided for selectively passing either the axial radiation or the radial radiation to the detector means. For example, with all mirrors shown in FIG. 2, the first mirror 36 may be fixed (or movable only for alignment), and the fourth mirror 60 may be mounted on a carriage to move the mirror in and out of the path of the axial radiation (in this case with angle A zero). As another example, the third and fourth mirrors may be omitted and the second mirror angled to reflect the radial radiation directly to the first mirror, albeit at a larger angle with the axis. In a further alternative, the third and fourth mirrors are omitted and the second mirror held at 45° to reflect the radial radiation parallel to the longitudinal axis, and the first mirror is replaced by an optical switch to select between the radiation paths. In any of these or other alternative embodiments, however, the plasma generator remains fixed, and optics are used to select modes.

Figure 3:
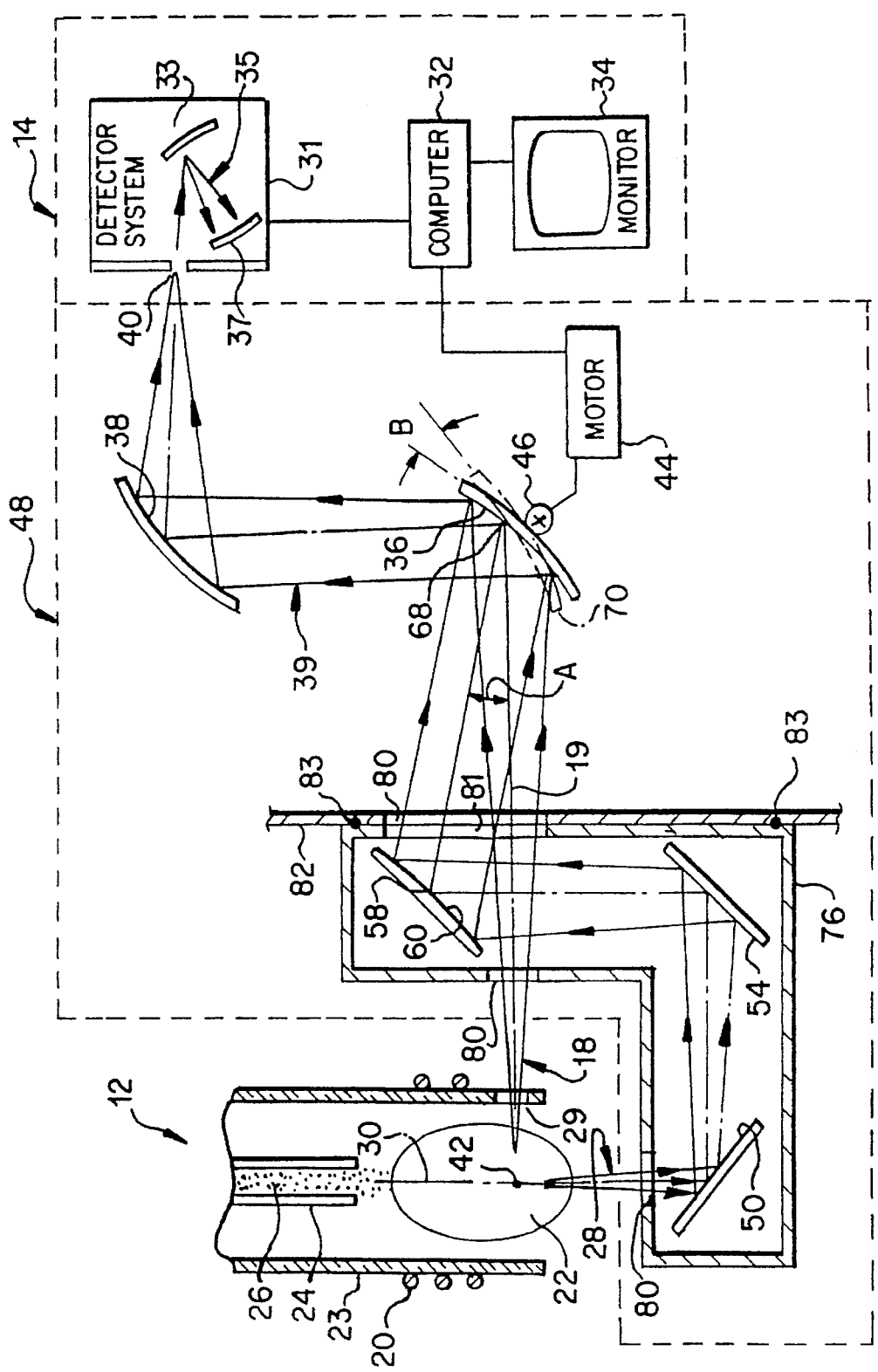
FIG. 3 is a drawing of another embodiment of an atomic emission spectrometer, similar to that of FIG. 2 with a different orientation for the plasma generator.

A further alternative arrangement (FIG. 3) reverses the paths of the axial and radial radiations to the first mirror. Such an aspect would have the ICP 12 rotated 90° from that shown in FIG. 2, so that the first mirror 36 receives the radial radiation 18 directly on the radial path line 19, and the axial radiation 28 is passed at a angle to the first mirror through the reflector means. The latter, in a preferred embodiment, is again formed of the second mirror 50, the third mirror 54 and the fourth mirror 60. The mirrors 50, 54 are preferably equidistant from the radial path line, with the fourth mirror 60 being offset from the radial path line 19 just outside of the radial radiation 18. Other components anti functioning of the system of FIG. 3 are the same as in FIG. 2, and are numbered accordingly.

Thus, more generally, either one of the axial radiation and the radial radiation is predetermined as a primary radiation on a linear path line, the path line being the longitudinal axis or the radial path. The other (radial or axial) then becomes predetermined as a secondary radiation. The first mirror is directly receptive of the primary radiation along the path line. The reflector means passes the secondary radiation to the first mirror at an angle to the path line, preferably as low an angle a possible. In the aspect of FIG. 2, the axial radiation 28 is the primary, and the radial radiation 18 the secondary. In the aspect of FIG. 3, the radial radiation 18 is the primary, and the axial radiation 28 is the secondary. In preferred embodiments for either aspect, the second mirror 50 and the third mirror 54 are equidistant from the path line, and the fourth mirror 60 is offset from the path line by the small angle.

While the invention has been described above in detail with reference to specific embodiments, various changes and modifications which fall within the spirit of the invention and scope of the appended claims will become apparent to those skilled in this art. The invention is therefore only intended to be limited by the appended claims or their equivalents.

We claim:

1. An atomic emission spectrometer comprising an induction coupled plasma generator for effecting light radiation and having a longitudinal axis, detector means with an entrance aperture for detecting the radiation relative to spectral wavelength, and an optical apparatus arranged cooperatively with the plasma generator and the detector means to pass radiation emitted from the plasma generator through the aperture to the detector means, wherein the radiation includes axial radiation emitted from the plasma generator along the longitudinal axis and radial radiation emitted from the plasma generator generally normal to the longitudinal axis, and the optical apparatus comprises optical selection means for selectively passing either the axial radiation or the radial radiation through the aperture to the detector means.

2. An atomic emission spectrometer comprising an induction coupled plasma generator for effecting light radiation and having a longitudinal axis, detector means for detecting the radiation relative to spectral wavelength, and an optical apparatus arranged cooperatively with the plasma generator and the detector means to pass radiation emitted from the plasma generator to the detector means, wherein the radiation includes axial radiation emitted from the plasma generator along the longitudinal axis and radial radiation emitted from the plasma generator generally normal to the longitudinal axis, the optical apparatus comprises optical selection means for selectively passing either the axial radiation or the radial radiation to the detector means, one of the axial radiation and the radial radiation is preselected as a primary radiation having a linear path line and the other is preselected as a secondary radiation, and the selection means comprises a rotatable first reflector spaced from the plasma generator on the path line so as to be directly receptive of the primary radiation, reflector means disposed to be receptive of the secondary radiation and pass the same to the first reflector at an angle different than that of the primary radiation, and rotating means for rotating the first reflector to a first orientation or to a second orientation, the first orientation being to reflect the primary radiation in to the detector means, and the second orientation being to reflect the secondary radiation in to the detector means.

3. The spectrometer of claim 2 wherein the angle is substantially as small as possible without the reflector means substantially interfering with the primary radiation.

4. The spectrometer of claim 3 wherein the reflector means comprises a second reflector disposed laterally from the path line so as to reflect secondary radiation from the plasma generator into a direction generally parallel to the path line toward the first reflector, a third reflector disposed laterally from the path line so as to reflect the radiation from the second reflector toward a central point proximate the path line between the plasma generator and the first reflector, and a fourth reflector disposed at the central point adjacent to the primary radiation without substantially interfering therewith so as to reflect the secondary radiation from the third reflector to the first reflector.

5. The spectrometer of claim 4 wherein the second reflector and the third reflector are each planar and oriented at a 45° angle to the path line.

6. The spectrometer of claim 4 wherein the first reflector is spaced from the plasma generator on the longitudinal axis, whereby the axial radiation is predetermined as the primary radiation and the radial radiation is predetermined as the secondary radiation.

7. The spectrometer of claim 4 wherein the detector means has an entrance aperture receptive of the radiation from the first reflector, a first optical path length for the primary radiation is defined from a selected emission point of radiation by the plasma generator to the aperture, a second optical path length for the secondary radiation is defined from the predetermined emission point to the aperture, the second path length being longer than the first path length, the optical apparatus includes a common focussing means for focussing to the aperture the primary radiation passed by the selection means from the emission point and for focussing to the aperture the secondary radiation passed by the selection means from the emission point, and the optical apparatus further comprises compensating means disposed for focussing to compensate for the second path length being longer than the first path length, such that the emission point and the aperture are conjugate foci for the axial radiation and for the radial radiation.

8. The spectrometer of claim 7 wherein the compensation means comprises the fourth reflector being convex.

9. The spectrometer of claim 7 wherein the common focussing means comprises the first reflector being concave, and further comprises a further concave reflector or a convex mirror optically disposed between the first mirror and the aperture.

10. The spectrometer of claim 4 wherein the path line intersects the first reflector at an axial point, the central point is on the fourth reflector central to the secondary radiation reflected by the fourth mirror, and the path line and a line extending between the axial point and the central point subtend an angle between about 1° and 10°.

11. The spectrometer of claim 10 wherein the angle subtended is between about 2° and 5°.

12. The spectrometer of claim 4 wherein the detector means has an entrance aperture receptive of the radiation from the first reflector, and the rotating means comprises first means for adjustment of the first mirror to align the axial radiation into the aperture when the first mirror has an orientation to reflect the axial radiation into the aperture, and second means for adjustment of the first mirror to select a position along the axis of an emission point of radiation for the radial radiation when the first mirror has an orientation to reflect the radial radiation into the aperture.

* * * * *

UNITED STATES PATENT AND TRADEMARK OFFICE
CERTIFICATE OF CORRECTION

PATENT NO. : 5,483,337
DATED : January 9, 1996
INVENTOR(S) : Thomas W. Barnard et al.

It is certified that error appears in the above-indentified patent and that said Letters Patent is hereby corrected as shown below:

Column 2, line 10, change "4,261,638" to -- 4,261,683--.

Column 4, line 54, after "mirror" insert -- 38 --.

Column 4, line 67, after "mirror" insert -- 36, --.

Signed and Sealed this

Eighteenth Day of June, 1996

Attest:

BRUCE LEHMAN

Attesting Officer  Commissioner of Patents and Trademarks